United States Patent [19]

Nakauchi et al.

[11] Patent Number: 5,124,069
[45] Date of Patent: * Jun. 23, 1992

[54] OPTICALLY ACTIVE SUBSTANCE AND LIQUID CRYSTAL COMPOSITION COMPRISING SAME

[75] Inventors: Jun Nakauchi, New York, N.Y.; Keiichi Sakashita, Kawasaki; Seiji Hayashi, Kawasaki; Yoshitaka Kageyama, Kawasaki; Yoshihiro Sako, Kawasaki; Tetsuya Ikemoto, Kawasaki, all of Japan

[73] Assignee: Mitsubishi Rayon Company Ltd., Japan

[*] Notice: The portion of the term of this patent subsequent to Sep. 3, 2008 has been disclaimed.

[21] Appl. No.: 493,559

[22] Filed: Mar. 14, 1990

[30] Foreign Application Priority Data

Mar. 16, 1989 [JP] Japan .................. 1-64879

[51] Int. Cl.⁵ .............. C09K 19/34; C09K 19/52; C07D 309/00
[52] U.S. Cl. .............. 252/299.61; 252/299.01; 549/273
[58] Field of Search .............. 252/299.61, 299.01; 549/273

[56] References Cited

U.S. PATENT DOCUMENTS 4,818,431  4/1989  Eidenschink .............. 252/299.61
5,045,228  9/1991  Nakauchi et al. .............. 252/299.61

Primary Examiner—Richard D. Lovering
Assistant Examiner—Cynthia Harris
Attorney, Agent, or Firm—Finnegan, Henderson, Farabow, Garrett & Dunner

[57] ABSTRACT

Disclosed is an optically active substance represented by the formula:

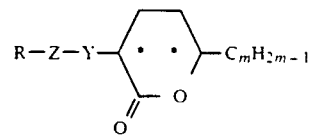

wherein m is an integer of 1 to 14, Y is

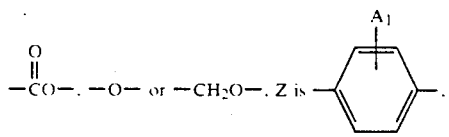

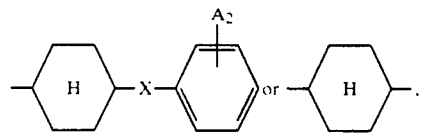

R is $-C_nH_{2n-1}$, $-OC_nH_{2n-1}$, $-OCOC_nH_{2n-1}$ or $-COOC_nH_{2n-1}$ (in which n is an integer of 1 to 18), each of the asterisked carbon atoms is an asymmetric carbon atom, X a single bond, $-CO_2-$, or $-OCO-$, and $A_1$ and $A_2$ is hydrogen, fluorine, chlorine, bromine, cyano or methoxy.

2 Claims, 1 Drawing Sheet

OPTICALLY ACTIVE SUBSTANCE AND LIQUID CRYSTAL COMPOSITION COMPRISING SAME

BACKGROUND OF THE INVENTION

Field of the Invention

The present invention relates to a novel optically active substance and a liquid crystal composition comprising this optically active substance.

The liquid crystals currently widely used in a liquid crystal display (LCD) are classified into the nematic phase, and since they are of the light-receiving type, the display system using these liquid crystals is characterized in that there is no eye fatigue therefrom and the power consumption is very low. Nevertheless, the display system using these liquid crystals has problems in that the response speed is low and the view angle of the display is narrow.

A display device or printer head using a ferroelectric liquid crystal having advantageous characteristics inherently possessed by nematic liquid crystals, such as no eye-fatigue property and very low power consumption, and having high response speed and high contrast comparable to those of display elements of the light-emitting type, has been investigated.

The ferroelectric liquid crystal was discovered for the first time by R. B. Meyer et al in 1975 [J. physique, 36, L-69 (1975)]. This ferroelectric liquid crystal is classified into the chiral smectic C phase (hereinafter referred to as "Sm*C phase"), and a typical compound of this ferroelectric liquid crystal is p-decyloxybenzylidene-p'-amino-2-methylbutyl cinnamate (hereinafter referred to as "DOBAMBC") represented by the following formula:

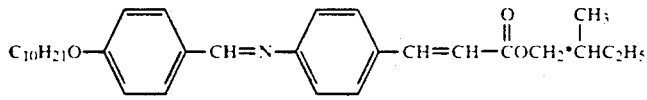

DOBAMBC and most of the ferroelectric liquid crystal materials proposed thereafter, have problems in that the temperature range showing the ferroelectricity (the temperature range in which the Sm*C phase is present) is narrow, and they cannot be used practically without an additive. Accordingly, attempts have been made to expand the temperature range showing the Sm*C phase of the lower and higher temperature sides, taking room temperature as the center, by mixing ferroelectric liquid crystals each other or with other liquid crystals. Under this circumstance, the development of a ferroelectric liquid crystal showing the Sm*C phase in the practical temperature range is desired. Furthermore, the development of a ferroelectric liquid crystal having a larger spontaneous polarization than those of the known ferroelectric liquid crystals is desired in the field of printer heads for which an ultra-high response speed is required.

When ferroelectric liquid crystals having the Sm*C phase are mixed, the kinds of applicable compounds (liquid crystals) are limited, and liquid crystal mixtures which give satisfactory various performances are difficult to obtain at present. Compounds having a Schiff base, such as DOBAMBC, have a poor light stability and a coloration thereof readily occurs.

SUMMARY OF THE INVENTION

Therefore, a primary object of the present invention is to provide an optically active substance which exhibits the Sm*C phase when incorporated in a composition having a smectic C phase (hereinafter referred to as "SmC phase"), which is chemically stable, is not colored, has an excellent light stability, and imparts large spontaneous polarization to a liquid crystal composition comprising this optically active substance.

Another object of the present invention is to provide a liquid crystal composition comprising this optically active substance as a part of the composition.

In accordance with the present invention, there is provided an optically active substance having a δ-valerolactone ring, which is represented by the following general formula (1):

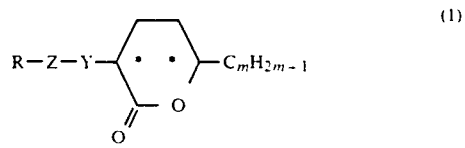

wherein m is an integer of from 1 to 14, Y represents

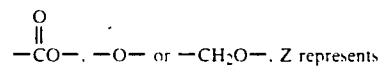

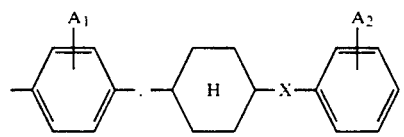

R represents $-C_nH_{2n+1}$, $-OC_nH_{2n+1}$, $-OCOC_nH_{2n+1}$ or $-COOC_nH_{2n+1}$ (in which n is an integer of from 1 to 18), each of the asterisked carbon atoms is an asymmetric carbon atom, X represents a single bond, $-CO_2-$, or $-OCO-$, and $A_1$ and $A_2$ independently represent a hydrogen atom, a fluorine atom, a chlorine atom, a bromine atom, a cyano group, or a methoxy group.

In accordance with the present invention, there is further provided a liquid crystal composition comprising at least one optically active substance represented by the above formula (1).

DESCRIPTION OF THE PREFERRED EMBODIMENTS

Figure 1:
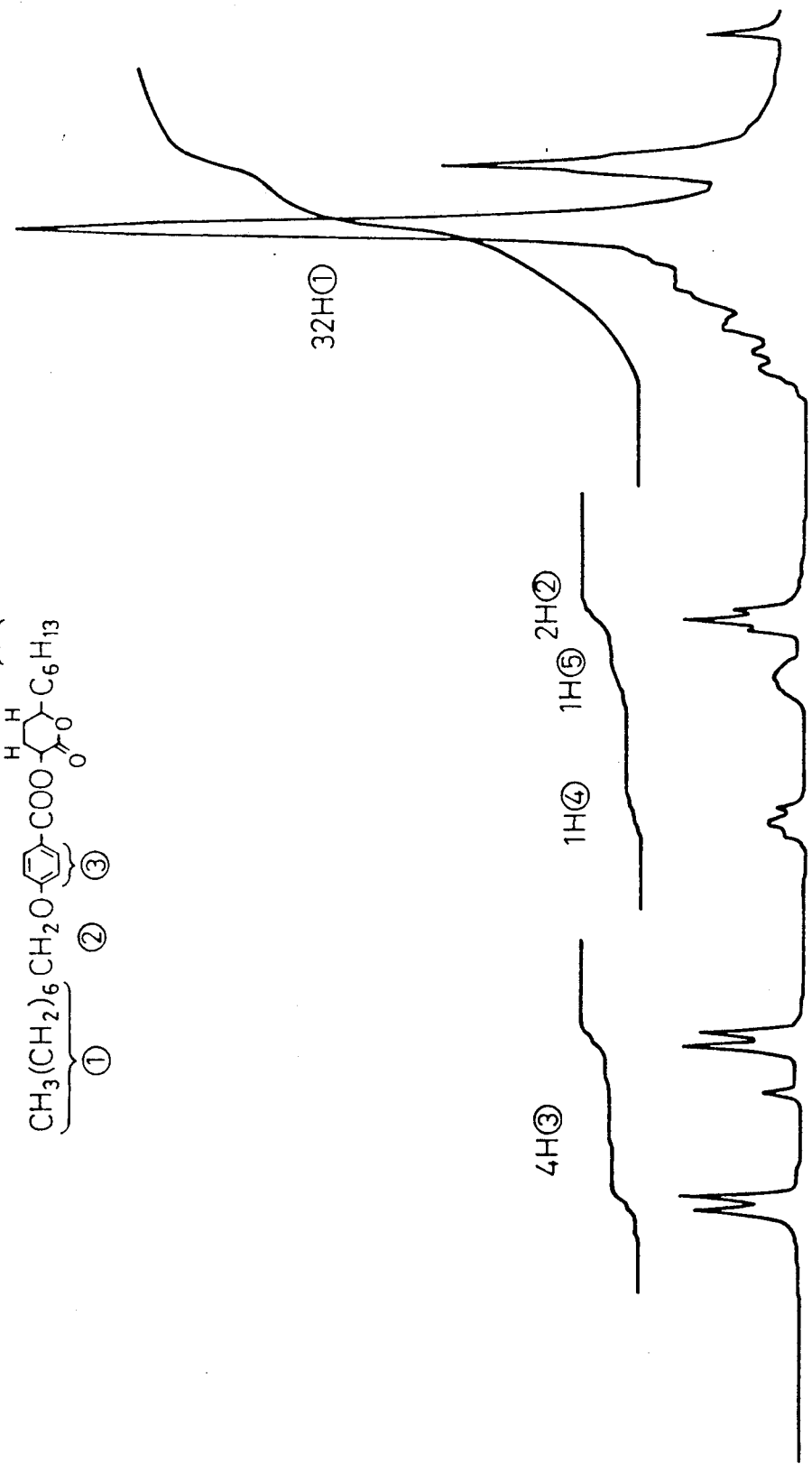
FIG. 1 illustrates the NMR spectrum of (2S,5R)-2-(4-octyloxybenzoyloxy)-5-hexyl-δ-valerolactone.

If the carbon number (n) of the alkyl group represented by R in formula (1) is 19 or larger, the purification of the starting materials used, such as

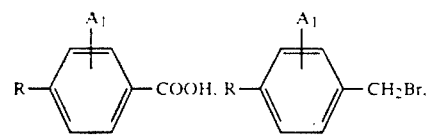

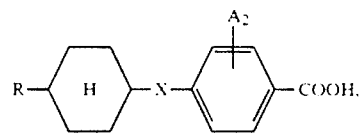

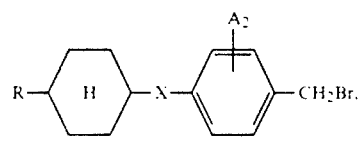

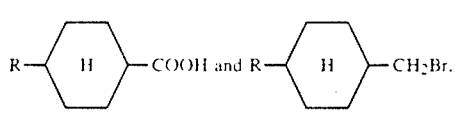

becomes relatively difficult. If the carbon number (m) of the alkyl group bonded to the lactone ring is 15 or larger, the purification of the optically active lactone becomes relatively difficult. In each case, the productivity is reduced, and when the optically active substance is mixed with other liquid crystal, the intensity of the spontaneous polarization tends to decrease.

The process for the synthesis of the optical active substance will now be described.

The 3-hydroxy-6-alkyl-δ-valerolactone of the following formula:

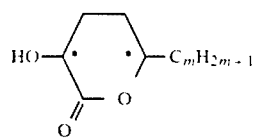

(1)

wherein m is an integer of from 1 to 14, which is used in the present invention, can be obtained by electrochemically synthesizing an optically active β-hydroxycarboxylic acid with a monoester of an optically active α-acetoxy-dibasic acid by Kolbe electrolysis and cyclizing the reaction product.

The optically active β-hydroxycarboxylic acid can be obtained, for example, by reacting a methyl alkyl ketone with diethyl carbonate in the presence of sodium hydride to form an ethyl ester of a β-ketocarboxylic acid and hydrolyzing the ethyl ester with potassium hydroxide, as indicated by the following reaction formula:

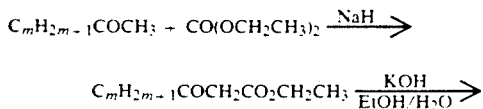

-continued $$C_mH_{2m-1}COCH_2CO_2K$$

and subjecting the carbonyl group at the β-position to the asymmetric reduction with baker's yeast to yield an optically active β-hydroxycarboxylic acid, as shown by the following reaction formula:

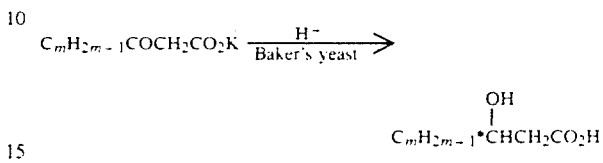

If the carbon number (m) of the alkyl group of the methyl alkyl ketone is 3 or smaller, the yield of the asymmetric reduction product in the above-mentioned process is not satisfactory, and therefore, preferably instead of the ethyl ester of the β-ketocarboxylic acid, and alkyl ester, having a larger carbon number (i.e., 6 or larger), of the β-ketocarboxylic acid is reduced.

Separately, S-(−)-malic acid is reacted with acetyl chloride and the obtained reaction product is reacted with anhydrous ethanol to yield an optically active monoethyl ester of α-acetoxydibasic acid, as represented by the following reaction formula [see Tetrahedron, 41, No. 13, 2751–2758 (1985)]:

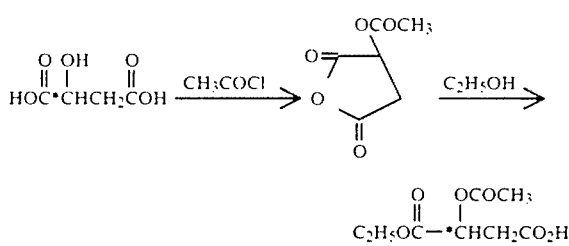

The obtained optically active β-hydroxycarboxylic acid is electrolytically reacted with the optically active monoethyl ester of α-acetoxydibasic acid to Kolbe electrolysis, as indicated by the following reaction formula:

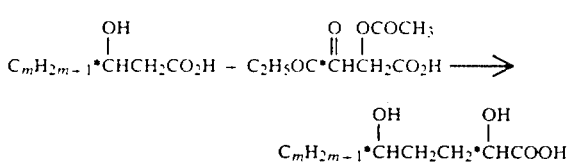

and the obtained product is cyclized in the presence of p-toluene-sulfonic acid to obtain the above-mentioned valerolactone derivative as shown by the following reaction formula:

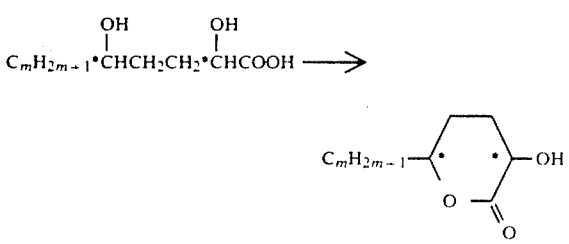

[Synthesis of Substance Represented by General Formula (1)]

The substance represented by General formula (1) can be synthesized through the following routes.

(a) Where Y is general formula (1) is —CO$_2$—, the synthesis route is expressed as follows:

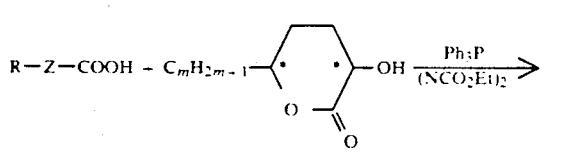

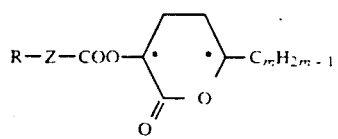

(b) Where Y in general formula (1) is —O—, the synthesis route is expressed as follows:

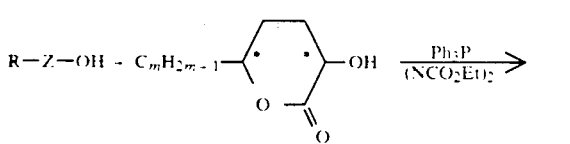

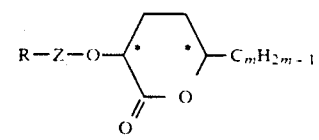

(c) Where Y in general formula (1) is —CH$_2$O—, the synthesis route is expressed as follows:

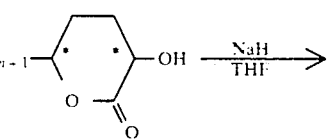

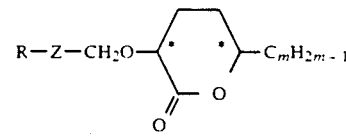

Since the optically active substance of the present invention does not possess an azomethine bond inherently possessed by the conventional ferroelectric liquid crystal substances, the substance of the present invention has a greatly improved chemical stability such as the hydrolysis resistance and an improved light stability, compared to the conventional cinnamic acid type compounds. Therefore, the substance of the present invention has excellent characteristics required for a display material.

The optically active substance of the present invention does not always show the chiral smectic C phase (hereinafter referred to as "Sm*C phase") alone, but the optically active substance of the present invention is characterized in that, when the substance is mixed with other liquid crystal substance having the Sm*C phase or other ferroelectric liquid crystal substance, the Sm*C phase is exhibited and the spontaneous polarization is increased, and therefore, the response time is shortened.

The liquid crystal composition of the present invention will now be described.

The liquid crystal composition of the present invention comprises at least one optically active substance of formula (1), but a composition comprising a plurality of ferroelectric liquid crystal substances, and optionally, an additive substance is advantageous over the liquid crystal composition comprising a single liquid crystal compound, because the applicable temperature rang can be broadened. As specific examples of other ferroelectric liquid crystal compound that can be mixed with at least one compound represented by general formula (1), the following compounds can be mentioned:

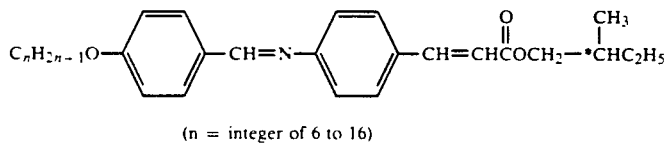

(n = integer of 6 to 16)

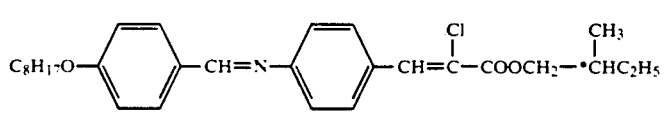

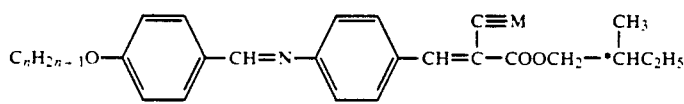

(n = 8 or 10)

-continued
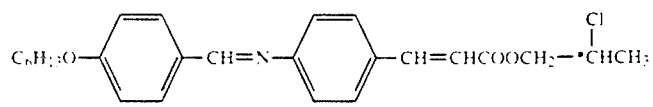
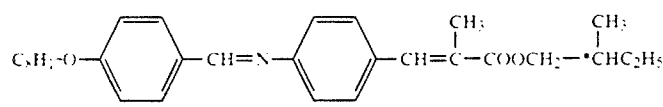
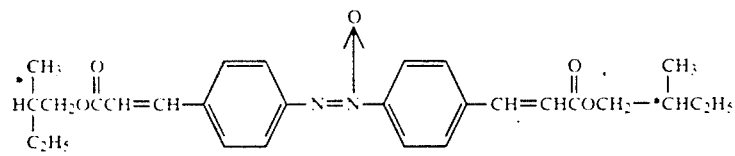
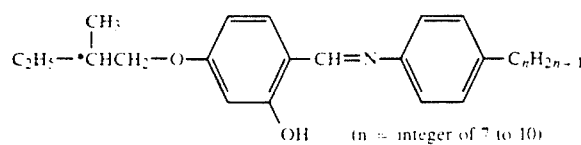
(n = integer of 7 to 10)
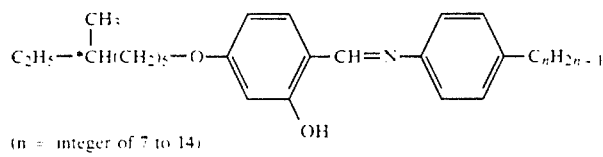
(n = integer of 7 to 14)
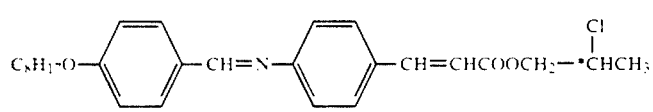
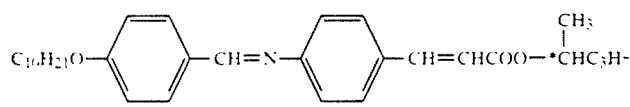
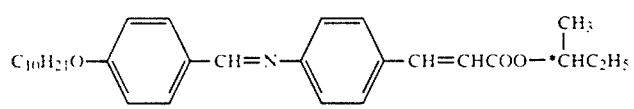
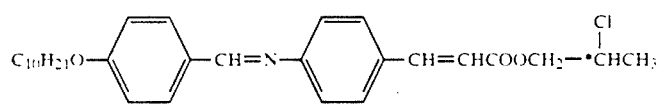
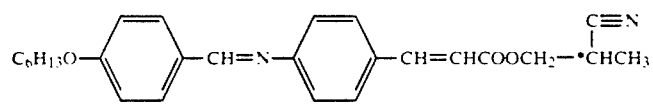
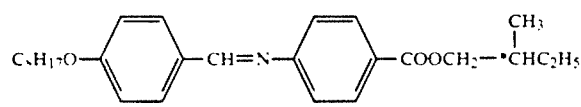
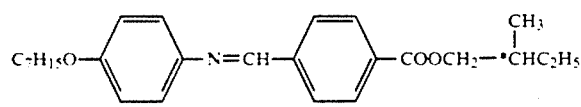
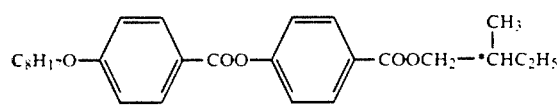

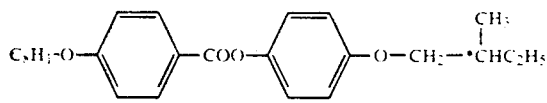

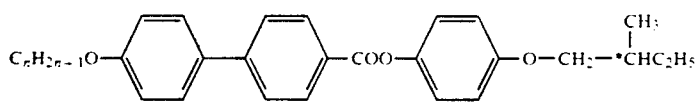

(n = integer of 6 to 14)

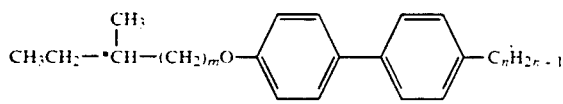

(m = integer of 2 to 5, n = integer of 8 to 12)

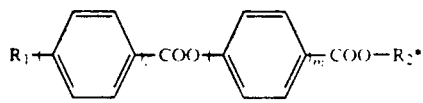

wherein l and m = 1 or 2, $R_1 = C_nH_{2n+1}O-$ or $C_nH_{2n+1}-$ (n = integer of 8 to 10)

and

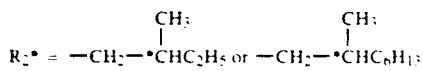

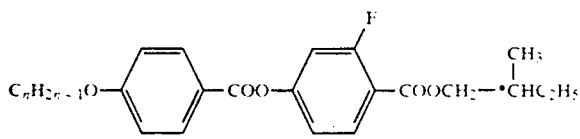

(n = integer of 8 to 18)

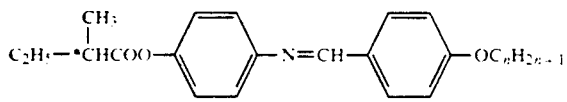

(n = integer of 7 to 11)

Other compounds can be mixed with the compounds of formula (1) and used in the form of liquid crystal compositions, if they are ferroelectric liquid crystal compounds.

If the compound of the present invention is mixed with a ferroelectric liquid crystal compound or composition showing the SmC phase, the mixture becomes a ferroelectric liquid crystal and as apparent from a high response speed, the mixture has a large spontaneous polarization.

Examples of the compound showing the SmC phase are described below, although other compounds and mixtures showing the SmC phase can be similarly used:

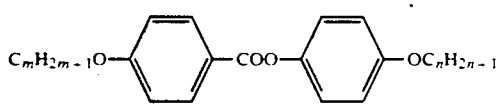

m = integer of 4 to 16, n = integer of 4 to 16

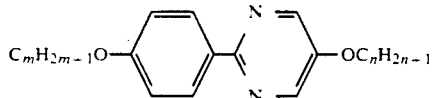

m = integer of 4 to 16, n = integer of 4 to 16

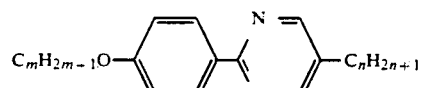

m = integer of 4 to 16, n = integer of 4 to 16

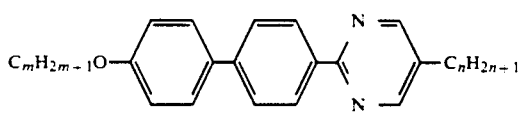

m = integer of 4 to 16, n = integer of 4 to 16

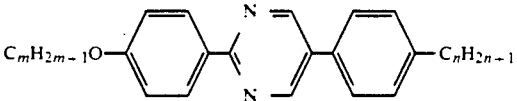

m = integer of 4 to 16, n = integer of 4 to 16

The present invention will now be described in detail with reference to the following examples.

REFERENTIAL EXAMPLE 1

Synthesis of β-hydroxynonanoic acid

To a solution comprising 210 ml of diethyl carbonate, 12.8 g of sodium hydride dispersed at a concentration of 60% by weight in an oil and 100 ml of dioxane was added dropwise a solution of 20.0 g of methyl ethyl ketone in 100 ml of dioxane in an argon atmosphere, the mixture was refluxed overnight, and the solvent was removed by distillation. The residue was subjected to distillation under a reduced pressure to obtain 20.0 g of ethyl hexylketoacetate (yield = 62.5%, boiling point 83° C. at 0.65 mmHg).

In a solution comprising 75 ml of ethanol, 75 ml of distilled water and 5.02 g of potassium hydroxide was dissolved 15 g of the obtained ethyl hexylketoacetate, and the solution was stirred at room temperature for 7.5 hours. Then, 3 l of distilled water, 360 g of sucrose and 168 g of dry yeast were added to the solution and the mixture was shaken at 30° C. for 16 hours. The liquid was filtered through Celite. The obtained solid was air-dried and extracted with ethyl acetate, and the extract was concentrated. Hydrochloric acid was added to the filtrate to adjust the pH value to 1, and sodium chloride was added to form a saturated solution. The solution was extracted with chloroform, and the extract and the above-mentioned ethyl acetate extract concentrate were dissolved in diethyl ether and the solution was extracted two times with a 1N aqueous solution of sodium hydroxide. Then, hydrochloric acid and sodium chloride were added to the aqueous solution of sodium hydrochloride to form a saturated aqueous solution of sodium chloride having a pH value of 1. The solution was extracted with ether five times, and the ether solution was recovered, washed with a saturated aqueous solution of sodium chloride and dehydrated on magnesium sulfate. Ether was evaporated, and the residue was dissolved in n-hexane and recrystallized therefrom to obtain 7.81 g of β-hydroxynonanoic acid [melting point = 49.3° to 50.0° C., $[\alpha]_D^{24.5} = -20.1°$ (C = 1.1, CHCL$_3$)].

REFERENTIAL EXAMPLE 2

Synthesis of β-hydroxybutanoic acid

In a liquid comprising 36 ml of absolute methanol and 36 ml of anhydrous 1,2-dichloroethane was suspended 5 g of optically active poly-β-hydroxybutyrate, and 1.1 ml of concentrated sulfuric acid was added to the suspension and the mixture was heated and refluxed for 57 hours. The mixture was cooled and a saturated aqueous solution of sodium chloride was added to the mixture. Then, the mixture was filtered through Celite. The filtrate was extracted with 70 ml of ethanol one time and with 20 ml of ethanol three times. The residue was washed with 100 ml of ether, and the ether used for this washing was combined with the above-mentioned extract. The mixture was washed with a saturated solution of sodium hydrogencarbonate and with a saturated aqueous solution of sodium chloride and was dried on magnesium sulfate. After the drying, ether was removed and the residue was subjected to distillation under a reduced pressure to obtain 4.0 g of ethyl (R)-β-hydroxybutanoate ($[\alpha]_D^{21.5} = -43.9°$).

In a liquid mixture comprising 15 ml of water, 15 ml of ethanol and sodium hydroxide was dissolved 4.0 g of ethyl (R)-β-hydroxybutanoate, and the solution was heated and refluxed for 3 hours and then cooled. Then, the solution was subjected to an ion exchange treatment with an ion exchange resin (Amberlite R120B supplied by Rohm & Haas). The solvent was removed by distillation under a reduced pressure to obtain 3.6 g of (R)-β-hydroxybutanoic acid.

REFERENTIAL EXAMPLE 3

Synthesis of 1-ethyl S-(2)-acetoxybutanedioate of the following formula:

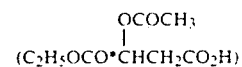

To 50 g of (S -(−)-malic acid was added 160 ml of acetyl chloride, the mixture was stirred and refluxed at 55° C. for 4 hours, and the solution was concentrated in vacuo. Then, 100 ml of benzene was added to the residue, and benzene and acetic acid were removed in vacuo by distillation. The residue was concentrated and cooled to room temperature, and 100 ml of absolute ethanol was added to the residue and the mixture was violently stirred while cooling now and then. The mixture was heated at 70° to 75° C. for 10 minutes and at 50° to 55° C. for 10 hours. Then, the solvent was removed from the mixture by distillation under reduced pressure, and the residue was separated and purified in a silica gel column by using methylene chloride/methanol (50/1) as the developing solvent to obtain 50.9 g of 1-ethyl S-(2)-acetoxybutanedioate [melting point = 50° to 51° C., $[\alpha]_D^{23} = -31.6°$ (C = 1.42, ethanol)].

REFERENTIAL EXAMPLE 4

Synthesis of (2S,5R)-2-hydroxy-5-hexyl-δ-valerolactone of the following formula and the like:

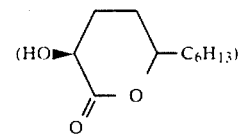

In methanol were dissolved 2.30 g of (R)-β-hydroxynonanoic acid and 7.90 g of 1-ethyl S-(2)-acetoxybutanedioate, synthesized in Referential Examples 1 and 3, respectively, and 230 mg of sodium methylate was added to the solution and the Kolbe hydrolysis was carried out at 20° to 30° C., 40 V and 1.5 A for 5 hours by using a constant voltage electrolysis apparatus (Model VE-8 supplied by Yanaco). After completion of the electrolysis, 60 ml of a 3N aqueous solution of sodium hydroxide was added to the solution, and the mixture was stirred overnight and methanol was removed. The residue was washed with ether, the alkaline aqueous solution was recovered, hydrochloric acid was added thereto adjust the pH value to 1, and sodium chloride was added to the liquid to obtain a saturated aqueous solution of sodium chloride. The solution was extracted with chloroform, and the extract was dehydrated on magnesium sulfate. Chloroform was evaporated, and the residue was dissolved in 10 ml of benzene and a catalytic amount of p-toluenesulfonic acid was added to the solution. The mixture was stirred at room temperature for 2 hours and dissolved in ether, and the solution was washed with a saturated aqueous solution of sodium bicarbonate three times and with a saturated aqueous solution of sodium chloride one time and was then dehydrated on magnesium sulfate. Ether was removed by evaporation and the intended product was separated and purified in a silica gel column by using a mixed solvent of n-hexane and ethyl acetate as the developing solvent and was recrystallized from a mixed solvent of n-hexane and ethyl acetate to obtain 310 mg of (2S,5R)-2-hydroxy-5-hexyl-δ-valerolactone. The melting point of the obtained compound was 75.5° to 77.0° C., and the elementary analysis values were as follows.

Elementary Analysis Values
Found values: C=65.84%, H=10.29%, N=0.06%
Theoretical values: C=76.32%, H=10.07%, N=0%

The specific rotation $[\alpha]^{25}$ of this compound was ±76.8° (in chloroform, C=1.1), and the results of the $^1$H-NMR analysis were as follows.

$^1$H-NMR, δ ppm: 4.36 (2H), 3.21 (1H), 1.31 (14H), 0.89 (3H).

(2S,5R)-2-Hydroxy-5-methyl-δ-valerolactone was synthesized in the same manner as described above except that β-hydroxybutanoic acid synthesized in Referential Example 2 was used instead of (R)-β-hydroxynonanoic acid.

REFERENTIAL EXAMPLE 5

Synthesis of 3-chloro-4-octyloxybenzoic acid of the following formula:

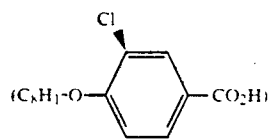

$(C_8H_{17}-O-\phantom{XX}-CO_2H)$

In 40 ml of ethanol were dissolved 10 g of 3-chlorohydroxybenzoic acid and 8 g of octyl bromide, and 40 ml a 2N aqueous solution of potassium hydroxide was added to the solution and the mixture was refluxed for 6 hours. The solution was made acidic and the precipitated crystal was recovered and recrystallized from an ethanol/water mixed solvent to obtain 9.5 g of 3-chloro-4-octyloxybenzoic acid.

Other 3-substituted-4-alkoxybenzoic acids were similarly synthesized.

REFERENTIAL EXAMPLE 6

Synthesis of monodecyl terephthalate

In 10 ml of dry benzene was dissolved 1.71 g of terephthaloyl dichloride, and 2.5 g of benzyl alcohol and 5 ml of triethylamine were added to the solution and reaction was carried out at room temperature with stirring overnight.

The reacted solution was poured into dilute hydrochloric acid cooled with ice, and the reaction product was extracted with ethyl acetate. The extract was washed with water and dried on magnesium sulfate. Then, ethyl acetate was evaporated and removed from the solution, and the residue was recrystallized from ethanol to obtain 3.2 g of benzyl terephthalate.

In 20 ml of acetone was dissolved 1.7 g of the obtained benzyl terephthalate, and a solution of sodium hydroxide in an amount equimolar to the above ester in a 1/1 water/ethanol mixed liquid was added to the above solution and the mixture was stirred overnight. Acetone was evaporated and removed from the solution, and dilute hydrochloric acid was added to the residue, and the liquid was extracted with ethyl acetate. The extract was washed with water and dried on magnesium sulfate, and ethyl acetate was evaporated and the residue was recovered and recrystallized from an acetone/water mixed solution to obtain 1.0 g of monobenzyl terephthalate. Then, thionyl chloride was added to 0.5 g of the obtained monobenzyl terephthalate to form an acid chloride. Then, unreacted thionyl chloride was removed by distillation under a reduced pressure. Then, 5 ml of pyridine and 0.31 g of decyl alcohol were added to the residue, and the mixture was stirred at room temperature to effect reaction. The reacted solution was poured into dilute hydrochloric acid cooled with ice, and the precipitate was recovered by filtration, dried and purified by the silica gel column chromatography to obtain 0.68 g of benzyldecyl terephthalate. The obtained compound was dissolved in an ethyl acetate/ethanol mixed solvent, 0.06 g of platinum black was added to the solution, and catalytic reduction was carried out under a hydrogen pressure of 1.8 kg/cm². The catalyst was removed by filtration and the solvent was removed from the reacted solution by distillation to obtain 0.48 g of monodecyl terephthalate.

REFERENTIAL EXAMPLE 7

Synthesis of 4-undecylcarboxybenzoic acid of the following formula:

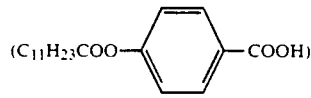

$(C_{11}H_{23}COO-\phantom{XX}-COOH)$

From 2.3 g of benzyl 4-hydroxybenzoate and 2.5 g of lauroyl chloride, 3.5 g of benzyl 4-undecylcarboxybenzoate was obtained according to customary procedures. The obtained compound was subjected to catalytic reduction under a hydrogen pressure of 2 kg/cm² by using platinum black as the catalyst to obtain 2.8 g of 4-undecylcarboxybenzoic acid.

EXAMPLE 1

In dehydrated benzene were dispersed 200 mg of (2S,5R)-hydroxy-5-hexyl-δ-valerolactone synthesized in the same manner as described in Referential Example 4, 250 mg of p-octyloxybenzoic acid and 200 μl of azodicarboxylic acid, and 270 mg of triphenylphosphine was added to the dispersion and reaction was carried out with stirring overnight. The reacted solution was concentrated, and the concentrate was separated and purified by the silica gel column chromatography using n-hexane/benzene as the developing solvent. The obtained product was recrystallized from methanol to obtain 180 mg of (2S,5R)-2-(4-octyloxybenzoyloxy)-5-hexyl-δ-valerolactone. The NMR spectrum of the obtained compound is shown in FIG. 1. The results of the measurement of the phase transition behavior by a differential thermal scanning calorimeter and a polarization microscope are shown below:

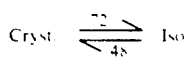

Cryst. means the crystal, and Iso represents the isotropic phase. The numerical figure given in the vicinity of the arrow is the temperature (°C.) of the transition to the corresponding phase.

EXAMPLES 2 THROUGH 9

Compounds were prepared in the same manner as described in example 1 except that a predetermined amount of a compound shown in Table 1 was used instead of 250 mg of p-octyloxybenzoic acid, and 100 mg of (2S,5R)-2-hydroxy-5-hexyl-δ-valerolactone was used, and the phase transition temperatures were examined. The results are shown in Table 1.

TABLE 1

| Example No. | Charged composition | | Obtained substance | Phase transition temperature (°C) |
|---|---|---|---|---|
| 2 | [lactone with OH, C6H13, C6H13 substituents] 100 mg; [benzoic acid with C8H17 substituent, COOH] 120 mg | | [ester product with C6H13, C8H17O, COO] 80 mg | Cryst $\xrightarrow{38}_{24}$ Iso |
| 3 | [lactone with OH, C6H13, C6H13] 100 mg; [Cl-substituted benzoic acid with C8H17O, CO2H] 150 mg | | [ester product with C6H13, Cl, C8H17O, COO] 90 mg | Cryst $\xrightarrow{50}_{26}$ Iso |
| 4 | [lactone with OH, C6H13, C6H13] 100 mg; [F-substituted benzoic acid with C8H17O, CO2H] 140 mg | | [ester product with C6H13, F, C8H17O, COO] 100 mg | Cryst $\xrightarrow{50}_{40}$ Iso |

TABLE 1-continued

| Example No. | Charged composition | | Obtained substance | Phase transition temperature (°C) |
|---|---|---|---|---|
| 5 | [lactone with OH and C6H13] 100 mg | [benzene with CH3O, C8H17O, CO2H] 140 mg | [lactone-benzene ester product with CH3O, C8H17O, C6H13] 60 mg | Cryst 45 ⇌ 25 Iso |
| 6 | [lactone with OH and C6H13] 100 mg | [benzene with C10H21OCO and COOH] 150 mg | [lactone-benzene ester with C10H21OCO, C6H13] 130 mg | Cryst 60 ⇌ 52 Iso |
| 7 | [lactone with OH and C6H13] 100 mg | [benzene with C11H23COO and COOH] 160 mg | [lactone-benzene ester with C8H17COO, C6H13] 120 mg | Cryst 97 ⇌ 92 Iso |

TABLE 1-continued

| Example No. | Charged composition | | Obtained substance | Phase transition (temperature °C.) |
|---|---|---|---|---|
| 8 | [structure: lactone with OH and C6H13] 100 mg | [structure: cyclohexane with H and C5H11] 120 mg COOH | [structure: lactone with cyclohexyl-COO and C6H13] 100 mg | Cryst ⇌ 93/82 Iso |
| 9 | [structure: lactone with OH and C6H13] 100 mg | [structure: phenyl-CO2 / cyclohexyl-CO2 with C5H11] 120 mg CO2H | [structure: lactone with phenyl-CO2-cyclohexyl-C5H11 and C6H13] 140 mg | Cryst ⇌ 143/114 Iso |

EXAMPLE 10 THROUGH 21

A liquid crystal composition A was formed by mixing the following components at mixing ratios shown below:

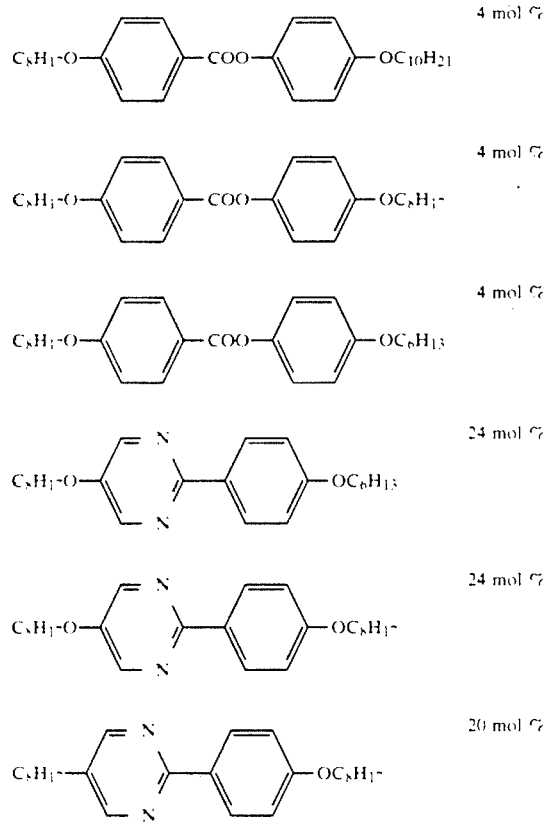

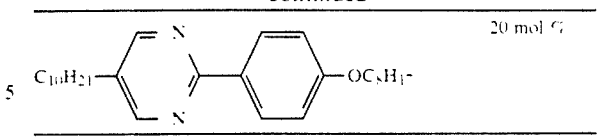

This composition A showed the following phase transition, but since the composition A was comprised only of optically unactive compounds, the composition was not a ferroelectric liquid crystal and did not show a spontaneous polarization:

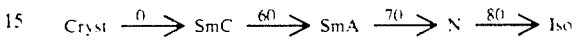

Note, SmC represents the smectic C phase, SmA represents the smectic A phase, and N represents the nematic phase.

This composition was mixed with a compound shown in Table 2 at a mixing ration shown in Table 2.

Some of the obtained compositions were independently cast in cells having a thickness of 2 μm, which were provided with transparent electrodes coated with a polyimide as the orientation treating agent, and subjected to a parallel orientation treatment by rubbing the surface.

Each element was arranged between two polarizers orthogonal to each other, and an electric field was applied. By application of a voltage of ±20 V, a change of the intensity of the transmitted light was observed. The response time was determined from this change, and the tilt angle was measured. The results are shown in Table 2.

As apparent from the results obtained in Examples 10 through 21, even if the substance of the present invention does not show a ferroelectric characteristic, when the substance is mixed with a compound showing the SmC phase, a ferroelectric composition having a good response characteristic is obtained.

TABLE 2

| Example No. | Compound incorporated in composition A - Structural formula | Mixing ratio (mol %) | Mixing ratio of composition A (mol %) | Phase transition temperature | Response time (μsec) | Tilt angle (deg) |
|---|---|---|---|---|---|---|
| 10 | C₈H₁₇—⌬—COO—[cyclohexanone with C₆H₁₃] | 5 | 95 | Cryst $\xrightarrow{1}$ Sm*C $\xrightarrow{60}$ SmA $\xrightarrow{68}$ N* $\xrightarrow{77}$ Iso | 1000 | 9 |
| 11 | C₈H₁₇—⌬—COO—[cyclohexanone with C₆H₁₃] | 20 | 80 | Cryst $\xrightarrow{2}$ Sm*C $\xrightarrow{52}$ N* $\xrightarrow{67}$ Iso | 380 | 15 |
| 12 | C₈H₁₇O—⌬(F)—COO—[cyclohexanone with C₆H₁₃] | 5 | 95 | Cryst $\xrightarrow{3}$ Sm*C $\xrightarrow{63}$ SmA $\xrightarrow{68}$ N* $\xrightarrow{76}$ Iso | 490 | 22 |
| 13 | C₈H₁₇O—⌬(F)—COO—[cyclohexanone with C₆H₁₃] | 20 | 80 | Cryst $\xrightarrow{3}$ Sm*C $\xrightarrow{49}$ N* $\xrightarrow{64}$ Iso | 240 | 19 |
| 14 | C₈H₁₇O—⌬(F)—COO—[cyclohexanone with C₆H₁₃] | 40 | 60 | Cryst $\xrightarrow{4}$ Sm*C $\xrightarrow{27}$ N* $\xrightarrow{48}$ Iso | 190 | 26 |
| 15 | C₁₀H₂₁OCO—⌬—COO—[cyclohexanone with C₆H₁₃] | 5 | 95 | Cryst $\xrightarrow{0}$ Sm*C $\xrightarrow{65}$ SmA $\xrightarrow{69}$ N* $\xrightarrow{76}$ Iso | 240 | 20 |

TABLE 2-continued

| Example No. | Compound incorporated in composition A | | Mixing ratio (mol %) | Mixing ratio of composition A (mol %) | Phase transition temperature | Response time (μsec) | Tilt angle (deg) |
|---|---|---|---|---|---|---|---|
| | Structural formula | | | | | | |
| 16 | C₁₀H₂₁OCO–⟨benzene⟩–COO– | ⟨δ-lactone with C₆H₁₃⟩ | 20 | 80 | Cryst →25→ Sm*C →67→ Iso | | |
| 17 | C₁₀H₂₁OCO–⟨benzene⟩–COO– | ⟨δ-lactone with C₆H₁₃⟩ | 40 | 60 | Cryst →45→ Sm*C →55→ Iso | | |
| 18 | C₈H₁₇–⟨cyclohexane⟩–COO– | ⟨δ-lactone with C₆H₁₃⟩ | 5 | 95 | Cryst →4→ Sm*C →59→ SmA →68→ N* →75→ Iso | | small |
| 19 | C₈H₁₇–⟨cyclohexane⟩–COO– | ⟨δ-lactone with C₆H₁₃⟩ | 20 | 80 | Cryst →3→ Sm*C →40→ SmA →64→ N* →69→ Iso | 3000 | 6 |
| 20 | C₈H₁₇–⟨cyclohexane⟩–COO– | ⟨δ-lactone with C₆H₁₃⟩ | 40 | 60 | Cryst →30→ SmA →53→ Ch →57→ Iso | 300 | |
| 21 | C₈H₁₇O–⟨benzene with Cl⟩–COO– | ⟨δ-lactone with C₆H₁₃⟩ | 5 | 95 | Cryst →3→ Sm*C →49→ SmA →66→ Ch →75→ Iso | 300 | 24 |

EXAMPLE 22

In 1 ml of dehydrated benzene were suspended 100 mg of (2S,5R)-2-hydroxy-5-hexyl-δ-valerolactone synthesized in the same manner as described in Referential Example 2 and 120 mg of 4-octyloxy-3-cyanobenzoic acid, and 0.1 ml of diethyl azodicarboxylate was added to the suspension with stirring at room temperature. Then, 150 mg of triphenylphosphine was added to the mixture and reaction was carried out overnight with stirring. The reaction mixture was concentrated under a reduced pressure and the residue was separated and purified by the silica gel column chromatography using an n-hexane/benzene (1/4) mixed solvent as the developing solvent. Recrystallization from ethanol gave 90 mg of (2R,5R)-(4'-octyloxy-3'-cyanobenzoyloxy)-5-hexyl-δ-valerolactone. When the phase transition behavior of the obtained compound was measured by a differential thermal scanning calorimeter and a polarization microscope, the following results were obtained:

$$Cryst \xrightleftharpoons{32.0} Iso$$

Note. Cryst. indicates a crystal and Iso indicates an isotropic phase, and the numerical figure given in the vicinity of the arrow shows the transition temperature (°C.) to the corresponding phase.

EXAMPLE 23

A crude product was obtained in the same manner as described in Example 22 except that (2S,5R)-2-hydroxy-5-hexyl-δ-valerolactone was used in an amount of 125 mg and 125 mg of p-hydroxybenzoic acid was used instead of 120 mg of 4-octyloxy-3-cyanobenzoic acid. The crude product was purified by the silica gel column chromatography to obtain 20 mg of (2R,5R)-2-(4'-pentyloxycarbonylphenoxy)-5-hexyl-δ-valerolactone.

EXAMPLE 24

The procedures of Example 23 were repeated in the same manner except that 180 mg of 4-(4'-pentylcyclohexyl)phenol and 100 mg of (2S,5R)-2-hydroxy-5-hexyl-δ-valerolactone were used, whereby 50 mg of (2R,5R)-2-[4-(4'-pentylcyclohexyl)-phenoxy]-5-hexyl-δ-valerolactone was obtained.

EXAMPLE 25

In 1.5 ml of dry dimethylformamide were dissolved 180 mg of octyl p-bromomethylbenzoate and 100 mg of (2S,5R)-2-hydroxy-5-hexyl-δ-valerolactone, and 300 mg of silver oxide was added to the solution and the mixture was stirred overnight at room temperature to effect reaction. After the reaction, diethyl ether was added to the reacted solution to extract the reaction product. The extract was washed with a saturated aqueous solution of sodium chloride and dried on anhydrous magnesium sulfate. Diethyl ether was removed by distillation under a reduced pressure. The obtained crude product was purified by the silica gel column chromatography to obtain 5 mg of (2S,5S)-2-(4'-octyloxycarbonylbenzyloxy)-5-hexyl-δ-valerolactone.

EXAMPLE 26 THROUGH 29

A liquid crystal composition B was obtained by mixing the following compounds at weight ratios shown below.

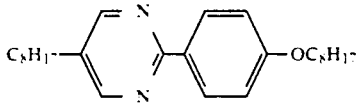

The composition B showed the following transition but since the composition was not optically active, the composition did not show a spontaneous polarization:

$$Cryst \xrightarrow{10} SmC \xrightarrow{52} SmA \xrightarrow{61} N \xrightarrow{65} Iso$$

Ferroelectric liquid crystal compositions were obtained by adding the compounds obtained in Examples 22 through 25 in amounts shown in Table 3 to the composition B. The phase transition temperatures, response times and tilt angles of these compositions are shown in Table 3.

TABLE 3

| Example No. | Compound incorporated in composition B | | Mixing ratio of composition B (mol %) |
|---|---|---|---|
| | Structural formula | Mixing ratio (mol %) | |
| 26 | 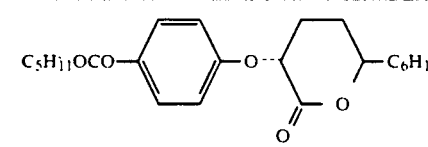 | 2 | 98 |

TABLE 3-continued

| Example No. | Phase transition temperature (°C) | Response time (0 to 50%) (μsec) | Tilt angle (deg) |
|---|---|---|---|
| 26 | Cryst —2.4→ Sm*C —44→ SmA —56.5→ N* —63.3→ Iso | 224 | 15 |
| 27 | Cryst —2.4→ Sm*C —49→ SmA —57.5→ N* —64.4→ Iso | 176 | 21 |
| 28 | Cryst —2.2→ Sm*C —45→ SmA —55.5→ N* —63.4→ Iso | 252 | 17.5 |
| 29 | Cryst —2.8→ Sm*C —46→ SmA —58.3→ N* —64.6→ Iso | 250 | 18 |

As apparent from the foregoing description, the optically active substance of the present invention is chemically stable, is not colored and has an excellent light stability, and therefore, the substance of the present invention is valuable as a component of a ferroelectric liquid crystal showing a large spontaneous polarization. Moreover, the liquid crystal composition of the present invention shows a ferroelectric characteristic in a broad temperature range including a practical temperature range, and as apparent from a high response speed thereof, the spontaneous polarization of the composition is large.

We claim:

1. An optically active substance having a δ-valerolactone ring, which is represented by the following general formula (1):

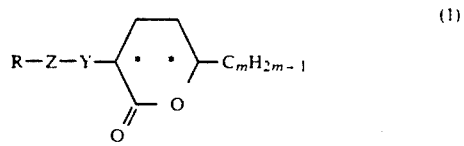

(1)

wherein m is an integer of from 1 to 14, Y represents —CO—, —O— or —CH$_2$O—, Z represents

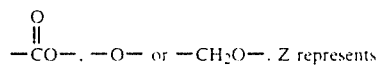

or

[cyclohexane ring with H]

R represents —C$_n$H$_{2n+1}$, —OC$_n$H$_{2n+1}$, —O-COC$_n$H$_{2n+1}$ or —COOC$_n$H$_{2n+1}$ (in which n is an integer of from 1 to 18), each of the asterisked carbon atoms is an asymmetric carbon atom, X represents a single bond, —CO$_2$—, or —OCO—, and A$_1$ and A$_2$ independently represent a hydrogen atom, a fluorine atom, a chlorine atom, a bromine atom, a cyano group, or a methoxy group.

2. A liquid crystal composition comprising at least one optically active substance represented by the formula (1) indicated in claim 1.

* * * * *

UNITED STATES PATENT AND TRADEMARK OFFICE
CERTIFICATE OF CORRECTION

PATENT NO. : 5,124,069

DATED : June 23, 1992

INVENTOR(S) : Jun Nakauchi, Keiichi Sakashita; Seiji Hayashi; Yoshitaka Kageyama; Yoshihiro Sako; Tetsuya Ikemoto It is certified that error appears in the above-identified patent and that said Letters Patent is hereby corrected as shown below:

Claim 1, column 31, in formula (1), approximately line 60, and in the abstract, line 3, "$C_mH_{2m-1}$" should read --$C_mH_{2m+1}$--.

Signed and Sealed this

Seventeenth Day of August, 1993

Attest:

BRUCE LEHMAN

Attesting Officer

Commissioner of Patents and Trademarks